United States Patent
Hansen et al.

(10) Patent No.: US 7,452,467 B2
(45) Date of Patent: *Nov. 18, 2008

(54) INDUCED SLUDGE BED ANAEROBIC REACTOR

(75) Inventors: Conly L. Hansen, Logan, UT (US); Carl S. Hansen, Garland, UT (US); Edward D. Watts, North Logan, UT (US); Kevin D. Pack, North Logan, UT (US)

(73) Assignees: Andigen, LLC, North Logan, UT (US); Utah State University, North Logan, UT (US)

( * ) Notice: Subject to any disclaimer, the term of this patent is extended or adjusted under 35 U.S.C. 154(b) by 162 days.

This patent is subject to a terminal disclaimer.

(21) Appl. No.: 11/272,293

(22) Filed: Nov. 10, 2005

(65) Prior Publication Data

US 2006/0065593 A1    Mar. 30, 2006

Related U.S. Application Data

(63) Continuation-in-part of application No. 11/155,283, filed on Jun. 17, 2005, now abandoned, which is a continuation of application No. 10/325,634, filed on Dec. 18, 2002, now Pat. No. 6,911,149.

(60) Provisional application No. 60/343,017, filed on Dec. 19, 2001.

(51) Int. Cl.
*C02F 3/28* (2006.01)

(52) U.S. Cl. .................. 210/603; 210/608; 210/188; 210/252

(58) Field of Classification Search ............... 210/603, 210/608, 614, 629, 143, 252, 522, 523, 525, 210/188
See application file for complete search history.

(56) References Cited

U.S. PATENT DOCUMENTS 2,889,929 A  *  6/1959  Kivell ................ 210/194
3,184,065 A  *  5/1965  Bradford ............ 210/519

(Continued)

FOREIGN PATENT DOCUMENTS

JP        64-22398    *   1/1989

*Primary Examiner*—Fred Prince
(74) *Attorney, Agent, or Firm*—Workman Nydegger

(57) ABSTRACT

An induced sludge bed anaerobic reactor includes a vessel in which a septum or other partition is positioned to maintain solids in wastewater being treated toward a lower zone in the reactor. A gas trap, which may also comprise an overpressure protection device, may be arranged at an outlet of the vessel. A distribution plate may be located at an inlet. A central aperture is formed in the septum into which a plug control mechanism, such as an auger, may be positioned to force solids to the lower zone of the reactor or, alternatively, pull solids up above the septum so that they can be removed from the vessel, if desired. A mixer may be utilized in connection with the bioreactor to mix the contents and prevent a crust from forming at the top of the bioreactor. Still further, a wall may be positioned to extend above the septum around its perimeter to assist in separating solids from the wastewater. The various types of bacteria used in the anaerobic process may also be separated, according to the present invention, in either a single vessel or multiple vessels so that the conditions of each respective vessel can be altered as desired.

39 Claims, 11 Drawing Sheets

U.S. PATENT DOCUMENTS

| | | | | |
|---|---|---|---|---|
| 3,622,009 A | * | 11/1971 | Bordner | 210/528 |
| 3,705,648 A | * | 12/1972 | Arvanitakis | 210/744 |
| 3,837,493 A | * | 9/1974 | Lin | 210/197 |
| 3,965,013 A | * | 6/1976 | Jackson | 210/519 |
| 4,208,279 A | * | 6/1980 | Varani | 210/613 |
| 4,302,329 A | * | 11/1981 | Pfefferkorn | 210/97 |
| 4,350,588 A | * | 9/1982 | Tsubota | 210/208 |
| 4,519,848 A | * | 5/1985 | Underwood | 134/34 |
| 4,609,460 A | * | 9/1986 | Vellinga | 210/188 |
| 4,840,732 A | * | 6/1989 | Rawlins | 210/306 |
| 5,338,447 A | * | 8/1994 | Vellinga | 210/195.1 |
| 5,441,634 A | * | 8/1995 | Edwards | 210/194 |
| 5,529,692 A | * | 6/1996 | Kubler | 210/603 |
| 5,747,311 A | * | 5/1998 | Jewell | 435/176 |
| 5,798,043 A | * | 8/1998 | Khudenko | 210/603 |
| 5,866,002 A | * | 2/1999 | Yates et al. | 210/601 |
| 6,592,751 B2 | * | 7/2003 | Haridas | 210/97 |

* cited by examiner

INDUCED SLUDGE BED ANAEROBIC REACTOR

RELATED APPLICATION

This is a continuation-in-part of U.S. patent application Ser. No. 11/155,283 filed 17 Jun., 2005, now abandoned, which is a continuation of U.S. patent application Ser. No. 10/325,634, filed Dec. 18, 2002, now U.S. Pat. No. 6,911,149, which claims priority, under 35 U.S.C § 119(e), from U.S. Provisional Patent Application Ser. No. 60/343,017, filed on 19 Dec. 2001, entitled "Induced Sludge Bed Anaerobic Reactor."

GOVERNMENT INTEREST

This invention was supported in part by the United States Government under Grant 68-3A75-3-153 (USDA-NRCS). The U.S. Government may have an interest in this application.

JOINT RESEARCH AGREEMENT

The invention disclosed herein was made under a joint development agreement between Andigen, a Utah limited Liability Company, and Utah State University, an institution of higher education.

FIELD OF THE INVENTION

This invention relates to anaerobic digestion of wastewater. More particularly, this invention relates to processes and devices to induce and control a sludge bed within an anaerobic reactor to enhance and improve the anaerobic digestion process.

BACKGROUND OF THE INVENTION

Wastewater treatment has always been important, particularly in agricultural production and food processing, which produces wastewater containing high concentrations of organic matter.

Anaerobic digestion is one traditional method of treating wastewater containing high concentrations of organic matter. Through anaerobic digestion, large quantities of organic matter are removed from the wastewater by converting the organic matter into biogas. Anaerobic digestion is particularly suitable for wastewater containing high concentrations of organics, such as wastewater generated through agricultural production and processing.

Inducing a sludge blanket or sludge bed (the terms "bed" and "blanket" are used interchangeably throughout this disclosure) has long been recognized as a way to promote anaerobic digestion. A sludge blanket is used to retain anaerobic bacteria in a designated space. One prior method of establishing such a sludge bed is to utilize a so-called upflow anaerobic sludge blanket (UASB), which causes a sludge blanket to form over time inside a bioreactor. There are many problems, however, with respect to prior UASBs. For example, it may take an extended period of time before the sludge blanket forms in a UASB. Traditional UASB bioreactors further do not have a method for controlling the formation of a sludge blanket within the reactor such that the sludge blanket may become too thick or otherwise less effective to carry out anaerobic digestion. Perhaps the biggest problem with traditional UASB bioreactors relates to plugging, which can be particularly problematic when treating wastewater containing significant amounts of solids, such as animal wastewater.

Still others have developed bioreactors wherein relatively high concentrations of bacteria are maintained by adding fixed media, such as plastic rings or rocks, which provide locations to which the bacteria can attach. Unfortunately, these prior types of bioreactors also plug often when treating substrates like animal manure and various kinds of food processing wastes.

There is a need, therefore, to provide a bioreactor that quickly forms a sludge blanket within the bioreactor. There is also a need to provide a bioreactor that can control the density of the sludge blanket to keep the bioreactor from plugging. Still another need exists to provide a bioreactor that has the ability to separate the various types of bacteria needed for the anaerobic breakdown of organics by forming gradients in a single sludge blanket reactor by providing separate tanks for the various stages of anaerobic digestion. Yet another need exists to provide a bioreactor that includes a device to assist in separating settling solids from the liquid or wastewater in which the settling solids are suspended. Another need exists recirculate any solids that do not break down, and to prevent effluent exiting the bioreactor from plugging. Another need exists to protect against overpressure of produced biogas.

SUMMARY OF THE INVENTION

The present invention relates to methods and apparatus for inducing and controlling a sludge blanket within an anaerobic reactor. In one embodiment, a rigid or semi-rigid partition or septum is positioned inside an enclosed bioreactor vessel. The septum tends to hold solids down or at least contain solid particles in the bottom zone of the bioreactor. The partition or septum may slope upwardly from the sides of the vessel toward a central aperture or hole so that biogas produced below the partition can move along the bottom of the septum and escape into the top of the tank where it can be removed. In addition, a plug control mechanism may be incorporated into the invention to force solids down below or pull solids above the partition or septum to control the amounts of solids retained in the bioreactor vessel. In one embodiment, the plug control mechanism comprises an auger with sloping fins to move solids from just above the hole in the septum downward to some distance beyond the bottom of the hole toward a lower zone in the bioreactor. Alternatively, the auger can pull sludge up through the hole and above the septum where the sludge can be removed from the vessel. Still further, a mixer may be attached to the shaft of the auger to mix the bioreactor contents and prevent a crust from forming at the top of the bioreactor. Also, a separator in the form of a weir wall may be incorporated into the vessel so that it extends above the septum and assists in separating solids from the wastewater being treated.

Yet another aspect of the invention involves using a single bioreactor or a plurality of bioreactors in connection with the present invention to further enhance separation. More specifically, a plurality of gradients in the sludge blanket may be formed in a single tank according to the various types of bacteria required for the stages of hydrolysis, acidogenesis, and methanogenesis in the anaerobic digestion process. Alternatively, multiple tanks may be utilized so that conditions in each tank can be adjusted according to the particular step being performed.

According to one aspect of the invention, an induced sludge blanket anaerobic reactor is provided and comprises a vessel, an inlet coupled to the vessel, the inlet introducing wastewater into the vessel, a first outlet coupled to the vessel, the first outlet directing wastewater to the outside of the vessel, a gas port coupled to the vessel, the gas port collecting gasses produced in the vessel, a septum having a periphery, the septum positioned within the vessel to maintain solid particles below the septum, and an aperture formed in the septum. The septum may taper from an apex to side walls of the vessel. The first outlet may be coupled to the side wall of the vessel at an elevation between the apex and the periphery of the septum at the side wall. The reactor may further comprise a second outlet coupled to the vessel adjacent to the first outlet. The second outlet may be coupled to the side wall of the vessel at a second elevation. The second elevation may be arranged between the first outlet and the periphery of the septum at the side wall. According to some aspects, the first and second outlets are fluidly connected in series to a recirculation pump capable of moving solids from above the septum back into the vessel below the septum. The first outlet may comprise a gas trap and overpressure device. The gas trap and overpressure device may comprise P-trap or an inverted P-trap. If an inverted P-trap is used, a center of a top of the inverted P-trap may be located at an elevation approximately equal to the apex. The inverted P-trap may have a cleanout as well. The gas trap and overpressure device may release gas through the first outlet at a predetermined pressure. The first outlet may comprise a passive gas trap and overpressure device, wherein the passive gas trap and overpressure device releases gas through the first outlet when gas pressure in the vessel above the septum reaches approximately ten to twenty inches of water. The passive gas trap and overpressure device may release gas through the first outlet when gas pressure in the vessel above the septum reaches approximately twelve inches of water. According to some embodiments, the reactor further comprises a distribution plate disposed in the vessel at the inlet. The inlet may comprise a pipe extended into the vessel to a tee, the tee emptying into the vessel in two directions, and the distribution plate may be disposed in the vessel at one exit of the tee. The distribution plate may be attached to a pedestal disposed in the vessel, the pedestal being attached to a floor of the vessel, wherein the pedestal is adjacent to but spaced from the inlet.

Another aspect of the invention provides an apparatus comprising an induced sludge blanket anaerobic reactor. The reactor comprises a vessel, an inlet coupled to the vessel, the inlet introducing wastewater into the vessel. The reactor also comprises a first outlet coupled to the vessel, the first outlet directing wastewater to the outside of the vessel. The first outlet comprises a gas trap. The reactor also comprises a gas port coupled to the vessel, the gas port collecting gasses produced in the vessel. The reactor includes a septum having a periphery, the septum positioned within the vessel to maintain solid particles below the septum, and an aperture formed in the septum inside the periphery. The reactor may comprise a second outlet in fluid communication with the first outlet, the second outlet disposed at a lower elevation on the vessel than the first outlet and located above the septum, wherein the gas trap comprises an inverted P-trap. The second outlet may lead to a recirculation pump in fluid communication with the vessel below the septum.

Another aspect of the invention includes an induced sludge blanket anaerobic reactor, the reactor comprising a vessel and an inlet coupled to the vessel. The inlet introduces wastewater into the vessel. The reactor includes a septum having a periphery, the septum positioned within the vessel to maintain solid particles below the septum. The reactor also comprises an aperture formed in the septum inside the periphery and a first outlet coupled to the vessel. The first outlet is arranged above the septum for directing wastewater to the outside of the vessel. The first outlet comprises a gas trap and overpressure device. A second outlet is coupled to the vessel at an elevation lower than the first outlet and above the septum. A gas port is coupled to the vessel and collects gas produced in the vessel. The reactor also includes a distribution plate inside the vessel at the inlet.

Another aspect if the invention provides a method of processing wastewater through anaerobic digestion. The method comprises sending a flow of wastewater into a vessel to hold wastewater, anaerobically digesting the wastewater with bacteria, retaining solids from the wastewater in a lower zone of the vessel with a septum, releasing gases generated in the lower zone of the vessel through an aperture in the septum, controlling plugging of the aperture, trapping gas at an effluent outlet to the vessel, collecting the gases generated in the lower zone of the vessel, and protecting against overpressure of the collected gases. The method may further comprise recirculating solids that pass through the aperture back to the lower zone.

Another aspect of the invention provides an induced sludge blanket anaerobic reactor. The reactor comprises a vessel and an inlet coupled to the vessel. The inlet introduces wastewater into the vessel. The reactor also includes a first outlet coupled to the vessel, the first outlet directing wastewater to the outside of the vessel. A gas port is coupled to the vessel, the gas port collecting gasses produced in the vessel. A septum is arranged substantially flat within the vessel, the septum maintaining solid particles therebelow. The septum is positioned within the vessel to maintain solid particles below the septum, and there is an aperture formed in the septum. The first outlet may comprise a downward sloping segment and an inverted P-trap extending from the downward sloping segment. A center of a top of the inverted P-trap is located at an elevation higher than the septum. A cleanout port may be disposed in the inverted P-trap according to some embodiments. The first outlet may also include a valved bypass downstream of the downward sloping segment and in fluid communication with the inverted P-trap.

Another aspect of the invention provides another induced sludge blanket anaerobic reactor. The reactor comprises a vessel, an inlet coupled to the vessel, a first outlet coupled to the vessel, a gas port coupled to the vessel, and a septum arranged within the vessel. The septum comprises an upward slope from a lowest portion to a side wall of the vessel and includes an aperture. The reactor may further comprise a plate disposed below and contacting the septum. The plate may comprise a generally flat plate including an aperture aligned with the aperture of the septum. The generally flat plate cooperates with the septum to enclose an area between the generally flat plate and a sloping surface of the septum.

The foregoing and other features, utilities, and advantages of the invention will be apparent from the following detailed description of the invention with reference to the accompanying drawings.

DETAILED DESCRIPTION OF THE INVENTION

The present invention relates to an anaerobic reactor 10 comprising an enclosure or vessel in which wastewater containing high concentrations of organic matter is introduced for treatment. An anaerobic reactor 10 according to the present invention is particularly applicable to wastewater generated through agricultural production and food processing.

In the anaerobic digestion process, bacteria convert carbon containing waste products, such as byproducts of farming, ranching, or food processing, into primarily biogas that is similar to natural gas. Suspended growth anaerobic digesters, such as lagoons or enclosed vessels, that are mixed and heated do not retain bacteria. Therefore, the rate of treatment depends on how fast the bacteria can grow.

An induced blanket bioreactor (IBR) quickly forms a sludge blanket or bed within the bioreactor. It is to be understood that the terms "sludge blanket" are synonymous and interchangeable with the terms "sludge bed." A sludge blanket refers to a zone or designated space within the bioreactor that is thick with solids. The sludge blanket initially consists of various types of solid particles naturally found in waste, such as undigested feed or pieces of bedding. A sludge blanket of this type is a haven for bacteria. The bacteria will attach to the particles of waste in the wastewater.

If the sludge blanket is controlled properly, the particles will grow without being flushed out of the bioreactor. Also, if the sludge blanket is managed properly, it will evolve to comprise mostly living bacteria, being made up of floating solids that trap bacteria. Where the solids, which consist mostly of living bacteria, are trapped in a zone, they multiply and consume the solid, non-living material that initially makes the blanket or that flows into the blanket. Without some type of sludge bed control mechanism, however, the wastewater passing through a continuously fed bioreactor would transport bacteria out of the bioreactor with the effluent. This is not desirable because a high concentration of bacteria is necessary to effectively destroy organic matter in the wastewater.

Prior bioreactors have been developed to provide a high concentration of bacteria to enhance the anaerobic digestion process. These prior bioreactors have added a fixed media, such as plastic rings or rocks, so that the bacteria have something to which they can attach. A drawback of these prior bioreactors, however, is that they soon plug when treating substrates, such as animal manure and many kinds of food processing wastes. They also employ no mechanism to control formation of the sludge blanket.

Figure 1:
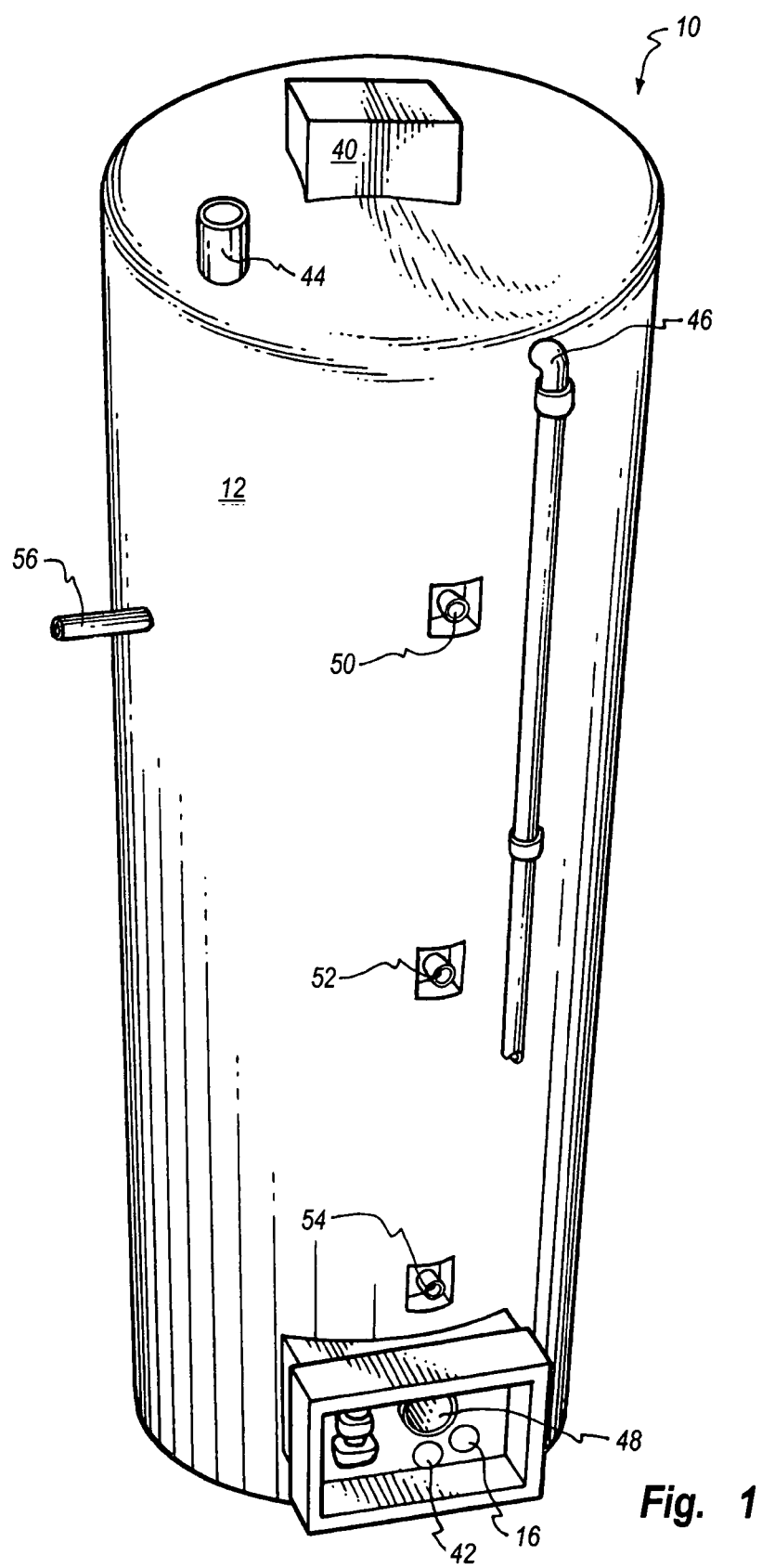
FIG. 1 is a perspective view of a bioreactor according to the present invention.
Figure 2:
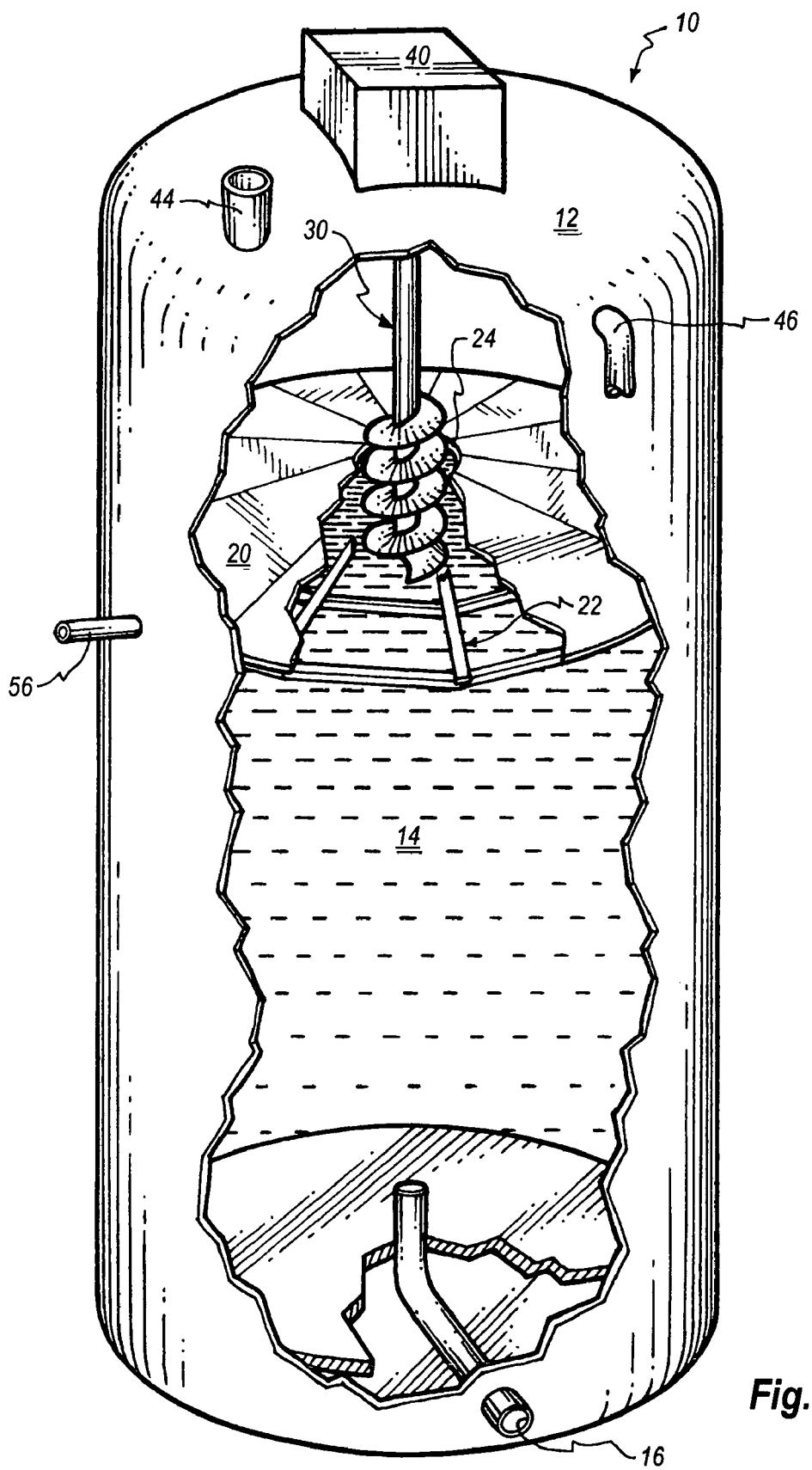
FIG. 2 is a front elevation view, including a broken away portion showing interior portions, of the bioreactor of FIG. 1.
Figure 3:
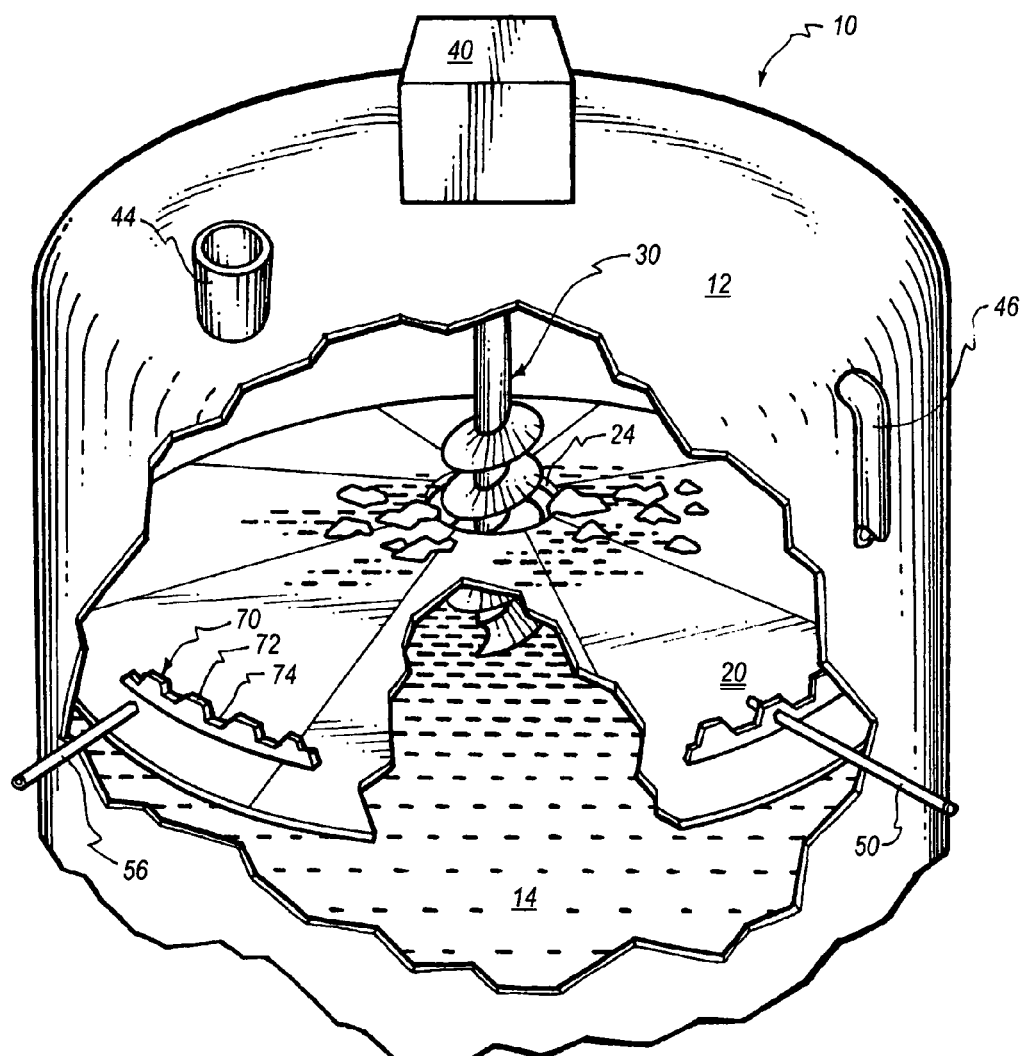
FIG. 3 is a partial perspective view showing the interior of the bioreactor including the sludge blanket control mechanism of the present invention.
Figure 4:
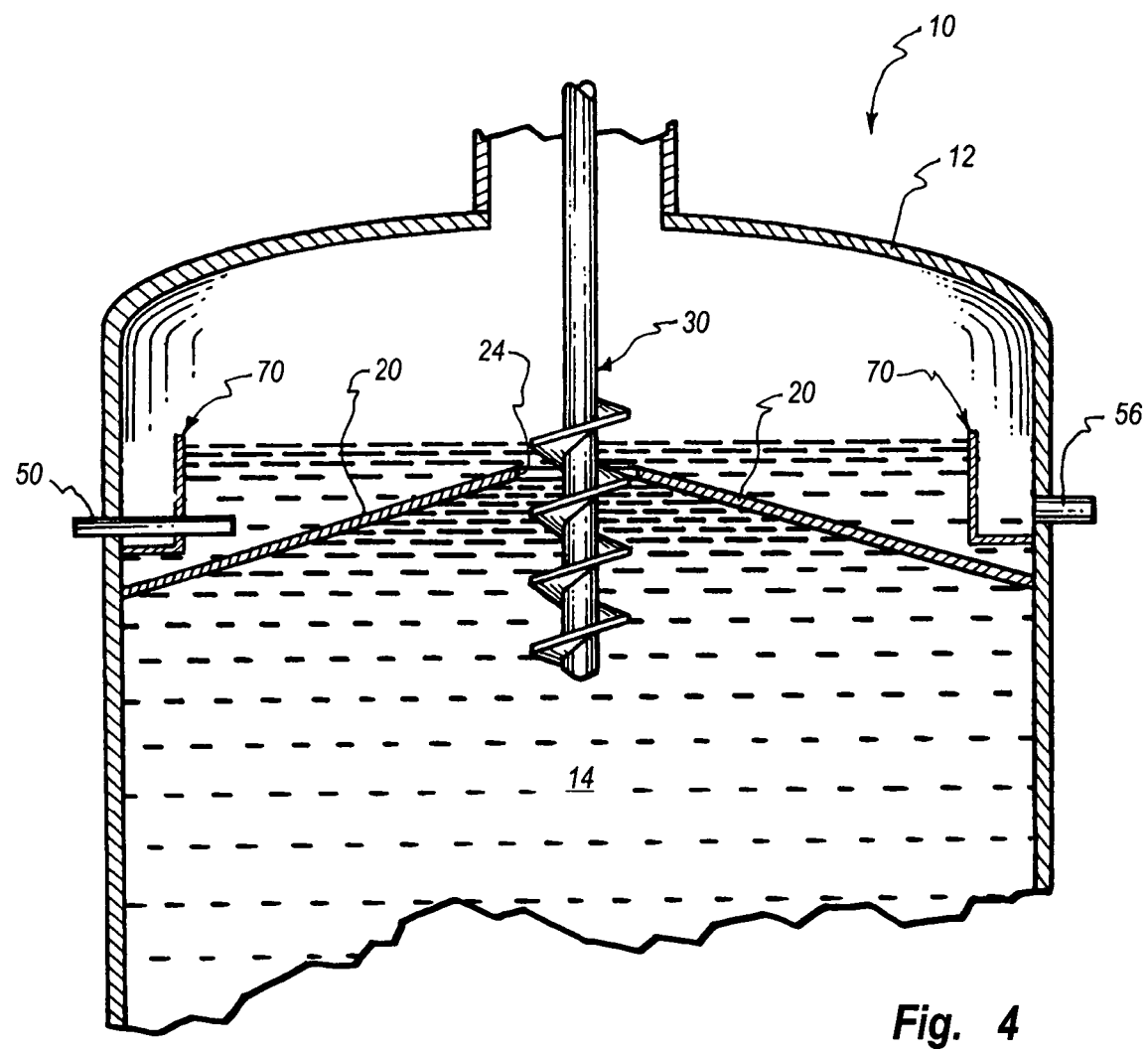
FIG. 4 is a partial sectional side elevation view of the bioreactor of FIG. 1 showing a weir wall secured to the walls of the bioreactor vessel.

Referring to FIGS. 1-3, the bioreactor 10 comprises a vessel or tank 12 which essentially comprises a cylindrical upstanding tank. The vessel 12 may be made of any suitable material, including but not limited to steel, plastic, or concrete. The vessel 12 provides an enclosure in which wastewater 14 is held. The vessel 12 is preferably round in cross section and two to five times taller than the diameter. The wastewater to be treated in vessel 12 may comprise any type of waste products, such as byproducts of farming, ranching, food processing, or any other type of wastewater that contains high concentrations of organic matter. The wastewater 14 is introduced into the central, bottom of vessel 12 through an inlet 16 (FIGS. 1 and 2). In one embodiment, the wastewater is introduced into the vessel 12 at a rate of approximately 10 gallons/minute.

As shown in FIGS. 2-6, a partition or septum 20 is positioned within or otherwise secured to the inside of the vessel 12 approximately two-thirds of the way up in vessel 12. The septum may be rigid or semi-rigid, and may comprise any suitable material, such as plastic, metal, or the like. Those skilled in the art will understand suitable materials for constructing the septum or partition 20. It is also to be understood that the septum 20 may comprise a plurality of panels, or may comprise a single, unitary piece of material. In one embodiment, the septum 20 is mounted inside of vessel 12 by a frame 22 which extends radially inwardly from the walls of vessel 12 toward the center of the vessel. Alternatively, the septum may itself be structurally sufficient to be secured to the inside of vessel 12 without a frame 22. The septum may slope upwardly from the vessel side walls toward an apex 80, and may include an aperture such as a central aperture 24. In one embodiment, the volume above the septum will be approximately one-third or less than the total volume of the bioreactor. The central aperture or hole 24 in the septum 20 will be approximately six inches, or approximately $1/10$ to $1/20$ of the diameter of the septum 20. The septum will further have approximately a one foot rise from the outer diameter of vessel 12 to the central aperture 24. The upwardly sloping bottom surface of septum 20 allows biogas to rise to the top of the vessel 12 where it can be removed.

A plug control device 30 is operatively coupled to the enclosure 12 and positioned within central aperture 24 in the septum 20. In one embodiment, the plug control mechanism is an auger 30 which will include sloping fins 32 (one continuously spiraling fin 32 is shown). When rotated clockwise, the auger 30 tends to force solids down toward a lower zone in vessel 12, or at least contain solid particles in the bottom zone of the bioreactor to promote the anaerobic digestion process. If the central aperture 24 becomes clogged or the wastewater 14 becomes too thick, the auger can be rotated counterclockwise to move particles up above the septum to clean out the central aperture 24. The auger 30 moves relatively thicker portions of the sludge blanket to the top of the partition or septum 20 where they can be taken out of the induced blanket reactor.

The plug control mechanism 30 is provided to prevent the aperture 24 from plugging, but it may help form and maintain the sludge blanket or sludge bed below the septum 20 to hold anaerobic bacteria within the bioreactor. By retaining the anaerobic bacteria within the sludge blanket area, there remain more bacteria for breakdown of the organics in a waste stream. By utilizing the plug control mechanism, wastewater can be treated much faster and much more efficiently in the apparatus described in connection with the present invention as compared to other prior bioreactors. This reduces capital costs, management required, and makes it easier to build and scale up. In one experimental use involving pig waste, treatment of the sludge blanket occurred approximately three to eight times faster than commonly used methods. The present invention also makes it much easier for an inexperienced operator to manage the anaerobic digester without having to know how the anaerobic digester actually works.

The auger 30 comprises a shaft 34 which is rotated by a motor or other type of drive mechanism (not shown) held inside a housing 40 (FIGS. 1 and 2). Housing 40 may also provide access to the interior of the bioreactor 10 to remove sludge, if desired, from the top of septum 20 (see FIG. 3).

With reference to FIG. 1, several different ports may be provided in the bioreactor 10. When sludge builds up toward the bottom of the bioreactor, a port 42 is provided for cleaning out unwanted, settled-out sludge. A top access port 44 (which may be of any suitable size) may be provided at the top of vessel 12 for added accessibility to the top of the enclosure. A vent or gas port 46 formed at the top of vessel 12 may be utilized to remove biogas generated within the bioreactor 10. A lower access port 48 (closed during normal operation), which can be of any suitable size, may be provided toward the lower end of the vessel 12 for access to the lower portion of vessel 12. A recirculation port 50 may be provided to redirect sludge or other wastewater above septum 20 to the lower portion or lower zone of the vessel 12, either through inlet 16 or through another return line (not shown). In the embodiments where a weir wall 70 (explained below) is utilized, the recirculation port 50 will extend through the weir wall so that it can access the area above septum 20 and inside weir wall 70 (FIGS. 3, 4, 6, and 8). Test ports 52, 54 may be provided to test the wastewater or sludge bed at any number of locations relative to the vertical orientation of the tank. An effluent port 56 may be provided to remove water that has passed through the continuously fed bioreactor. Preferably, water passing through effluent port 56 will be treated wastewater that contains little or no bacteria. Those skilled in the art will understand that any number of other ports may be utilized in connection with the present invention without departing from the scope or spirit thereof.

Figure 5:
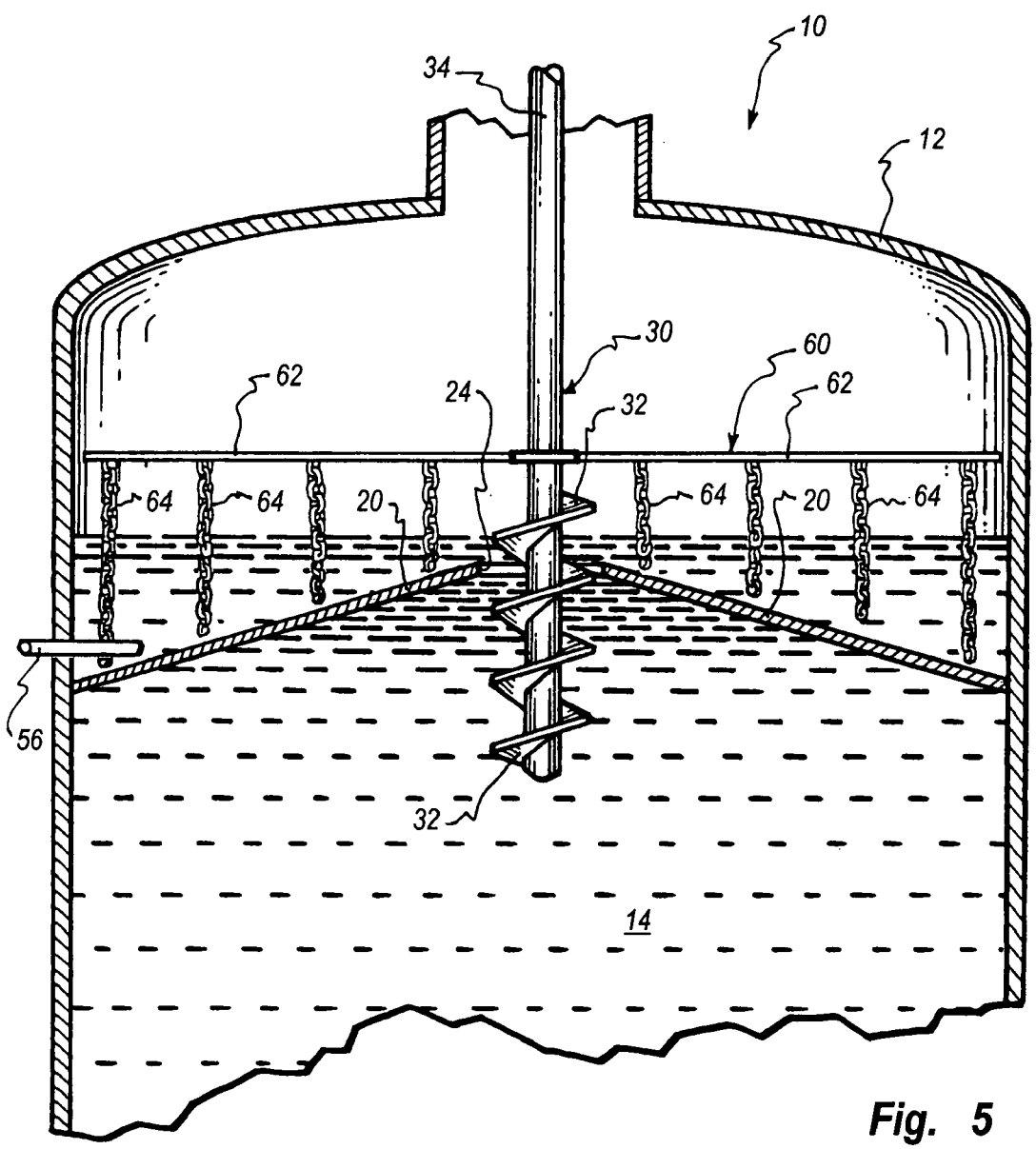
FIG. 5 is a partial sectional side elevation view of the bioreactor of FIG. 1 showing an alternative embodiment that includes a mixer to keep a crust from forming on top of the sludge bed.
Figure 6:
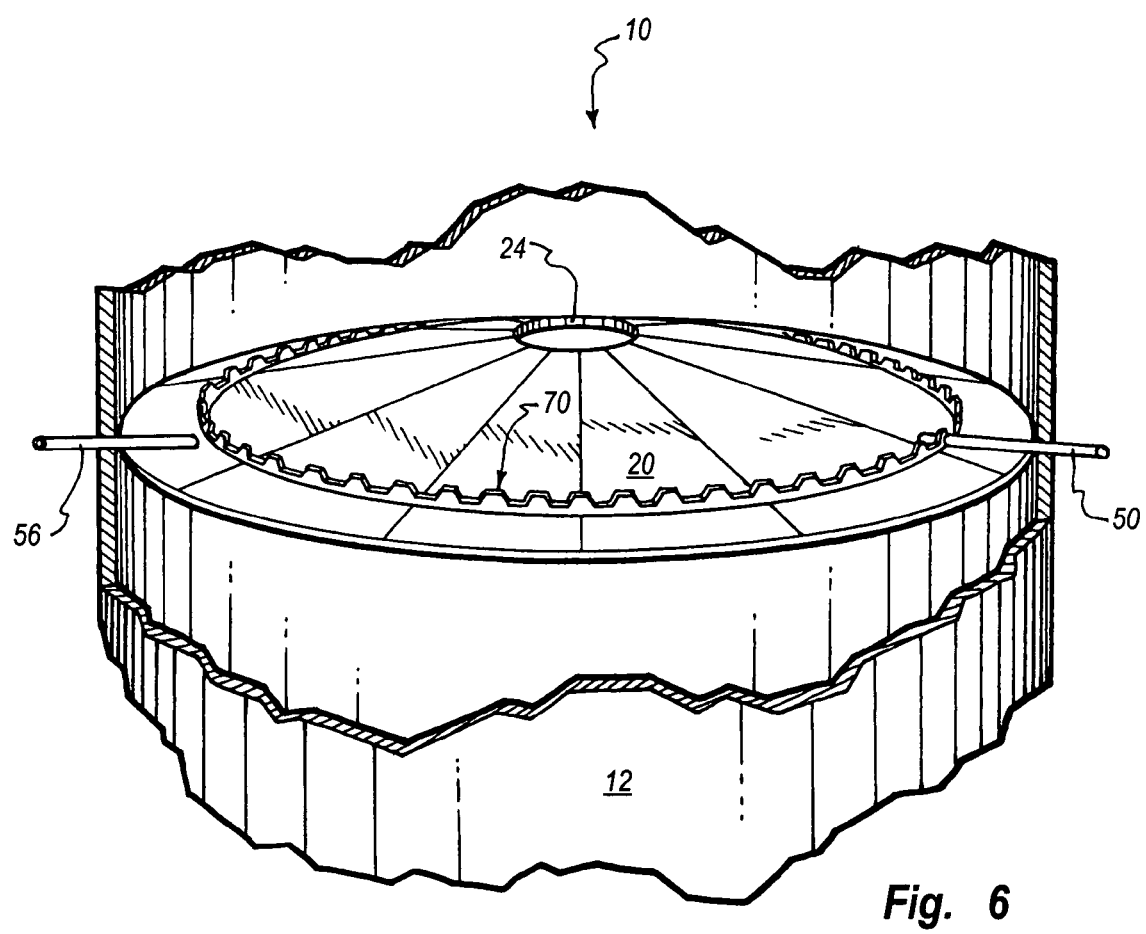
FIG. 6 is a partial sectional perspective view of the septum according to the present invention further including a weir wall to assist in separation of solids from the wastewater being treated within the bioreactor.

As shown in FIG. 5, a mixer 60 may be incorporated into the bioreactor 10 according to the present invention. In one embodiment, the mixer 60 comprises a pair of horizontally disposed bars or other members 62 coupled to the auger shaft 34. A plurality of metal chains 64 may be coupled to the horizontal bars 62. The chains 64 hang down into the top of the sludge bed. When the auger shaft 34 is rotated, chains 64 mix the bioreactor contents and prevent a crust from forming at the top of the bioreactor. It is to be understood that the chains 64 may be made of any suitable material and may be of any desirable length. In addition, although the embodiment of FIG. 5 shows the horizontal bars 62 and the chains 64 positioned above septum 20, it is to be understood that this or another type of mixer could be positioned below the septum 20, if desired.

Figure 8:
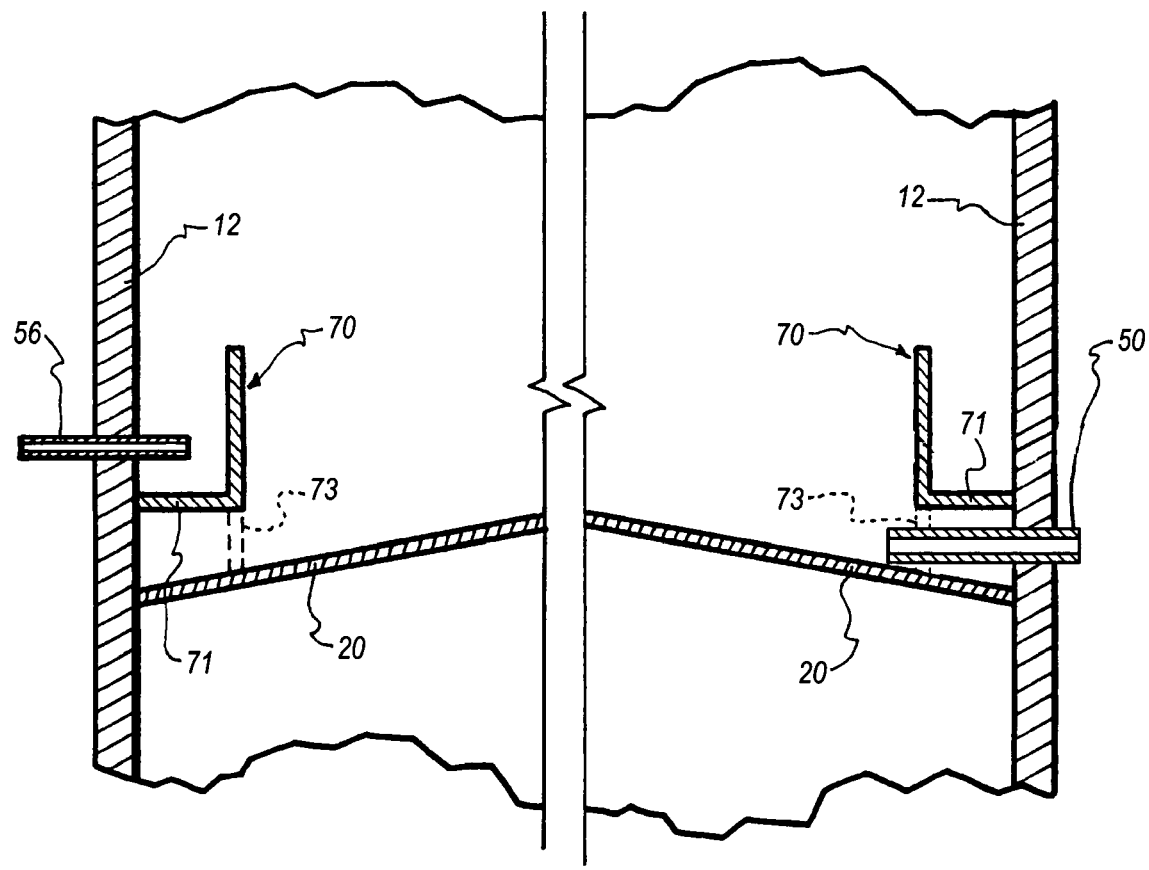
FIG. 8 is a partial sectional side elevation view of the septum and weir wall coupled to the enclosure or vessel according to the present invention.

Still another embodiment of the present invention relates to a weir wall 70 (FIGS. 3, 4, 6, and 8) that is coupled to and extends upwardly from the septum 20. The weir wall 70 is a solid vertical partition or wall that could be six inches high and extend entirely around the perimeter of the tank. The weir wall may, but does not have to, be placed close to the outside wall. As shown in FIG. 8, the weir wall 70 may be secured directly to the vessel wall 12 by a perpendicularly extending wall 71 (i.e., similar to a rain gutter) or, alternatively, by an extension section 73 (shown in dashed lines) that attaches directly to the septum 20.

The purpose of the weir wall is to provide a final mechanism to capture solids that would otherwise escape through effluent port 56. The septum and gravity will, in most cases, retain most of the solids within the bioreactor. Thus, in an ideal configuration only treated water without suspended solids will pass over the weir wall 70 and into effluent pipe 56. The top of the wall comprises a weir of some type, such as a jagged-edge weir, which is the type often used in settling tanks to separate solids from the liquid in which they are suspended. Such a jagged edge of weir wall 70 may include upwardly extending teeth portions 72 and lower trough portions 74. It is to be understood that any tooth configuration may be used on the top of weir wall 70.

The weir wall captures solids that somehow make it past the sludge blanket control mechanism 30 through the central area 24 of septum 20. This may occur because biogas attaches temporarily to some particles making them extremely buoyant. These solids contain a high concentration of bacteria and also contain undigested organic matter. They may be returned to the sludge bed via central aperture 24 in the septum or, alternatively, removed by means of a separate pipe (e.g., return duct 50) and an appropriate recycle pump. Water that passes over the weir wall 70 may be removed from the vessel 12 through effluent pipe 56 for further processing or disposal. It is to be understood that a weir wall 70 may or may not be used in connection with the present invention, depending on the circumstances and the wastewater being treated.

Operation of the induced sludge bed anaerobic reactor will be with a programmable logic controller (PLC) or microprocessor. The computer language will be one unique to PLC and will be understood by those skilled in the relevant art.

Still another aspect of the present invention relates to separation of the various types of bacteria needed for the anaerobic breakdown of organics by forming gradients in the sludge bed. The anaerobic digestion process is complex involving various types of bacteria that work symbiotically, each playing a role in the breakdown of organics. The stages of anaerobic digestion can be broken down into hydrolysis, acidogenesis, and methanogenesis. Specific types of bacteria are required for each stage of the process, and are well known to those skilled in the art. In a properly operating anaerobic digester, hydrolyzing bacteria break down large molecules that are then further broken down by acidogens into volatile organic acids (VOA). VOA is consumed by the methanogens, which produce methane as a byproduct. Acidogens are faster growing than those types of anaerobic bacteria in most situations. This means that most anaerobic digesters must be relatively lightly loaded to prevent the acidogens from outgrowing the methanogens and thus producing more VOA than the methanogens can consume. If they do not, the pH will drop into the acid range, which inhibits methanogens and builds up acid in a downward spiral until no acids are removed and the digester fails. This means that a limited amount of substrate (i.e., organic matter in wastewater) can be added to most anaerobic digesters in any given time period so that processes of hydrolysis and acid production do not outstrip the ability of methanogens to utilize the VOA and thus the pH will be maintained near the neutral range and the system is kept in balance.

Figure 7:
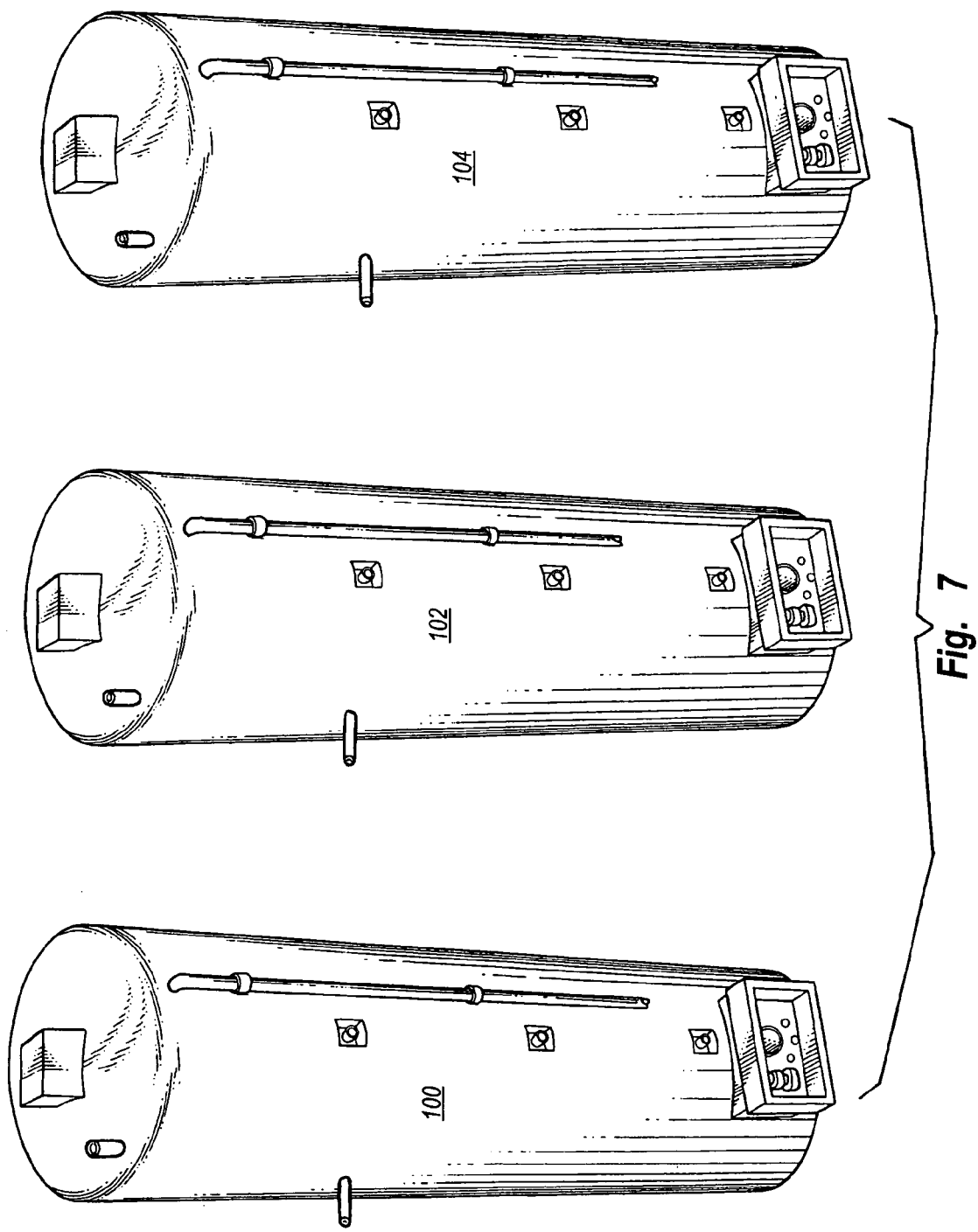
FIG. 7 is a perspective view of multiple tanks for controlling the respective environments for the various stages in the anaerobic process.

A single tank or multiple tanks may be utilized in connection with the induced sludge bed anaerobic reactor system according to the present invention. A multiple tank arrangement (e.g., tanks 100, 102, and 104 in FIG. 7) provides advantages for better separation of bacteria types. The multiple tank arrangement also facilitates easy upscaling, quick startup if the system needs servicing, and easier diagnosis and refurbishment if operating below parity. For example, hydraulic retention time (HRT) is longer and pH is higher in the methane-forming tank. Extensive control mechanisms may be used to maintain different conditions. In a multiple bioreactor tank arrangement, acidogens and methanogens may be captured in a settling basin/weir wall arrangement at the top of each separate bioreactor tank. Captured bacteria are returned to their respective sludge beds.

In the single tank system, the hydrolyzing and acid forming bacteria are captured toward the bottom of the induced blanket. Methanogens are also retained where they grow best, which is above the acidogens in the upper part of the sludge bed in a single tank. Anaerobic treatment may also be important for the production of usable energy, such as electricity, by utilizing the biogas produced in the anaerobic digestion process as fuel in an engine generator.

Figure 9:
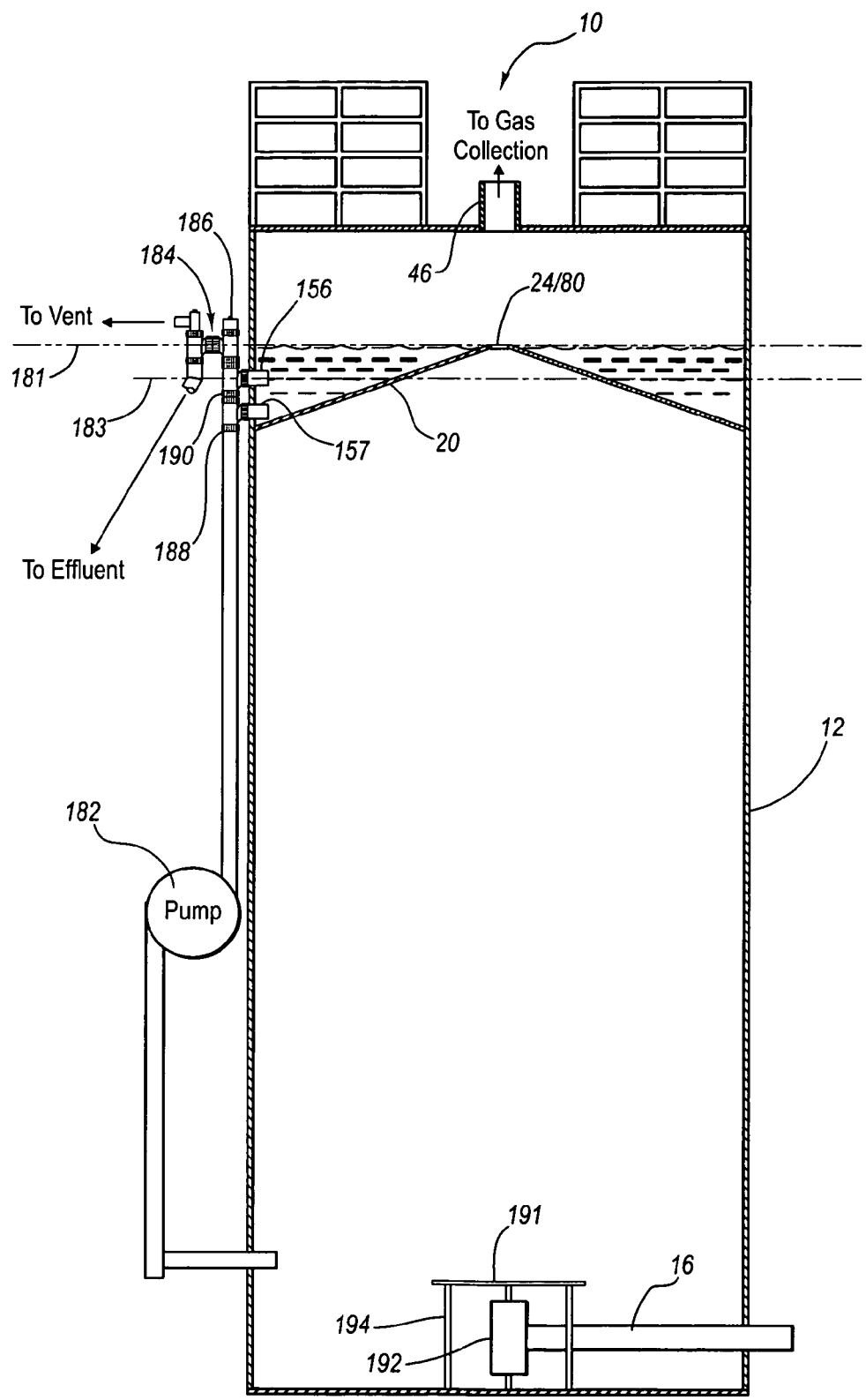
FIG. 9 is side elevation view, partly in section, of a bioreactor with a gas trap and overpressure device according to another embodiment of the present invention.
Figure 10A:
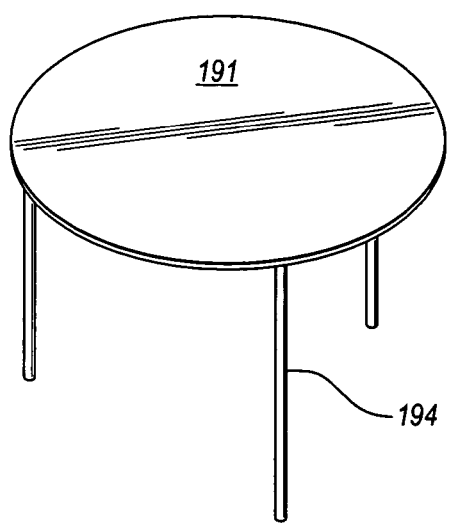
FIG. 10A is perspective view of a distribution plate and pedestal that may be added to the bioreactor of FIG. 9 at an inlet according to one embodiment of the present invention.
Figure 10B:
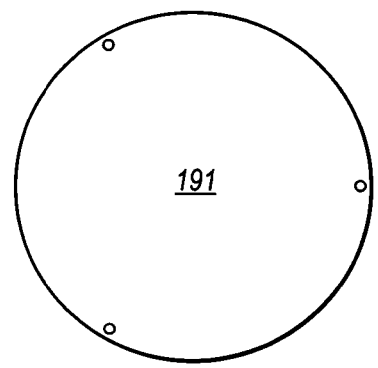
FIG. 10B is a top view of the distribution plate of FIG. 10A.
Figure 10C:
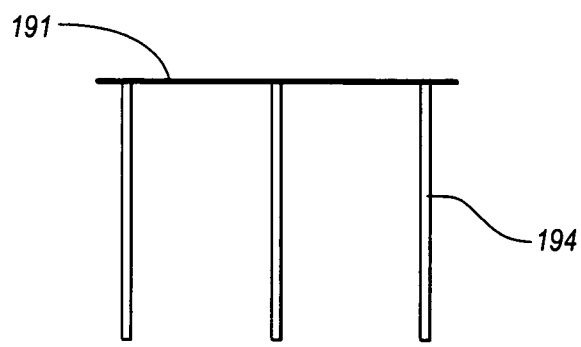
FIG. 10C is a side elevation view of the distribution plate of FIG. 10A.

Another embodiment of the present invention is shown in FIG. 9. The embodiment of FIG. 9 is similar or identical to the embodiment of FIGS. 1-6, and may include additional or modified piping at a first outlet. The first outlet may comprise an effluent port 156 coupled to the vessel 12. As with the effluent port 56 of FIG. 1, the first effluent port 156 directs processed wastewater to the outside of the vessel 12. The first effluent port 156 is coupled to the vessel at an elevation between the apex 80 of the septum 20 and the periphery of the septum 20 where the septum 20 meets the side walls of the vessel 12.

In addition, a second outlet may be coupled to the vessel 12 as well. As shown in FIG. 9, the second outlet comprises a second effluent port 157 and is coupled to the vessel 12 at a second elevation. The second elevation may be between the first effluent port 156 and the periphery of the septum 20 where the septum 20 meets the side walls of the vessel 12. Thus, the second effluent port 157 may be arranged just above the periphery of the septum. Any solids that may pass through the aperture 24 (FIG. 2) of the septum 20 will tend to sink along the septum toward the second effluent port 157.

The first and second effluent ports 156, 157 may be arranged in series as shown in FIG. 9, and may be fluidly connected to a pump such as a recirculation pump 182. The recirculation pump 182 may be turned on at will or at intervals and may be used to move any solids that pass through the aperture 24 (FIG. 2) back into a lower zone of the vessel 12 below the septum 20 for further processing. According to some embodiments, the recirculation pump 182 is piped back into the lower zone of the vessel 12 just under the septum 20. For example, the piping downstream of the recirculation pump 182 may be lead into the vessel 12 zero to thirty six inches under the septum 20.

The first outlet may include a gas trap or a combination gas trap and overpressure device. The gas trap or gas trap and overpressure device may comprise a P-trap, for example an inverted P-trap 184. The inverted P-trap 184 may reduce the risk of plugging as compared to a conventional P-trap. A centerline 181 of the top of the inverted P-trap 184 may coincide with the top of the apex 80. Therefore, liquids that have passed through the aperture 24 and sit on the top of the septum 20, tend to flow into the first and second effluent ports 156, 157, and out of the vessel 12 through the inverted P-trap 184. Solids will tend to "fall out" of the liquids toward the recirculation pump 182, mostly via the second effluent port 157, rather than potentially plugging the inverted P-trap 184. The centerline 181 of the top of the P-trap 184 may be arranged approximately ten to twenty inches above a centerline 183 of the first effluent port 156. For example, the centerline 181 of the top of the P-trap 184 may arranged approximately twelve inches above a centerline 183 of the first effluent port 156. However, according to some embodiments, the centerline 181 of the top of the P-trap 184 may arranged approximately one to three inches above a centerline 183 of the first effluent port 156.

The submerged first and second effluent ports 156, 157 and the inverted P-trap 184 prevent produced biogas from venting or leaving the vessel 12 through the effluent piping under normal circumstances. Instead, biogas is directed through the gas port 46 (FIG. 1). In addition, the inverted P-trap 184 protects against biogas overpressure. If biogas pressure within the vessel 12 increases to a predetermined measurement, the pressure will cause the fluid level on the septum 20 to decrease and expose the first effluent port 156 to the biogas. The excess pressure is then vented to atmosphere, maintaining the integrity of the vessel 12. According to some embodiments, the predetermined pressure that will expose the first effluent port 156 is approximately one to twenty inches of water (corresponding to the distance between the centerlines 181, 183 of the P-trap and the effluent port 156, minus the radius of the first effluent port 156). According to some embodiments, the predetermined pressure is approximately ten to twenty inches of water, or approximately twelve inches of water.

According to some embodiments, the P-trap 184 is equipped with a cleanout 186 to allow an operator access to the interior of the P-trap in the unlikely event of a plug or for other reasons. Moreover, according to some embodiments, there is no recirculation pump 182 or associated piping, and there may be a cleanout at a bottom 188 of a tee of the second effluent port 157 to facilitate removal of any accumulated solids. Further, according to some embodiments, both the recirculation pump 182 and the second effluent port 157 are omitted, and a cleanout may be located at the bottom of a tee 190 or other fall out collector of the first effluent port 156.

According to some embodiments, the septum 20 may be significantly raised from the side walls of the vessel 12 to the apex 80. For example, the elevation between the periphery of the septum 20 and the apex 80 may be approximately ten to twenty inches or twelve to eighteen inches. However, according to other embodiments, the elevation between the periphery of the septum 20 at the walls of the vessel 12 and the apex 80 may be quite shallow. For example, according to some embodiments, the elevation between the periphery of the septum 20 and the apex 80 may be approximately one to three inches. A more flat or shallow septum 20 may facilitate higher bacteria concentrations in the vessel 12 by holding more of the bacteria in the lower zone of the vessel 12.

Referring next to FIGS. 9 and 10A-10C, according to some embodiments, a distribution plate may 191 be disposed in the vessel 12 at the inlet 16. The inlet 16 of the embodiment of FIG. 9 includes a tee 192 that tends to cause the wastewater to empty into the vessel 12 in two directions. Wastewater that tends to drop to the bottom the vessel 12 is distributed by the floor of the vessel. Wastewater that tends to exit the tee 192 through the top is distributed by the distribution plate 191.

Accordingly, the distribution plate 191 may be located in close proximity to the top outlet of the tee 192.

The distribution plate 191 may be metal, plastic, or other material and may comprise any shape, including the circular shape shown. The distribution plate 191 may be supported by a pedestal 194 that may comprise, for example, three legs. The pedestal 194 may be attached to the distribution plate 191 in any manner, and the pedestal 194 may be integral with the distribution plate 191 as well. The pedestal 194 may be welded or otherwise attached to the floor of the vessel 12 to maintain the position of the distribution plate 191 relative to the tee 192.

Figure 11:
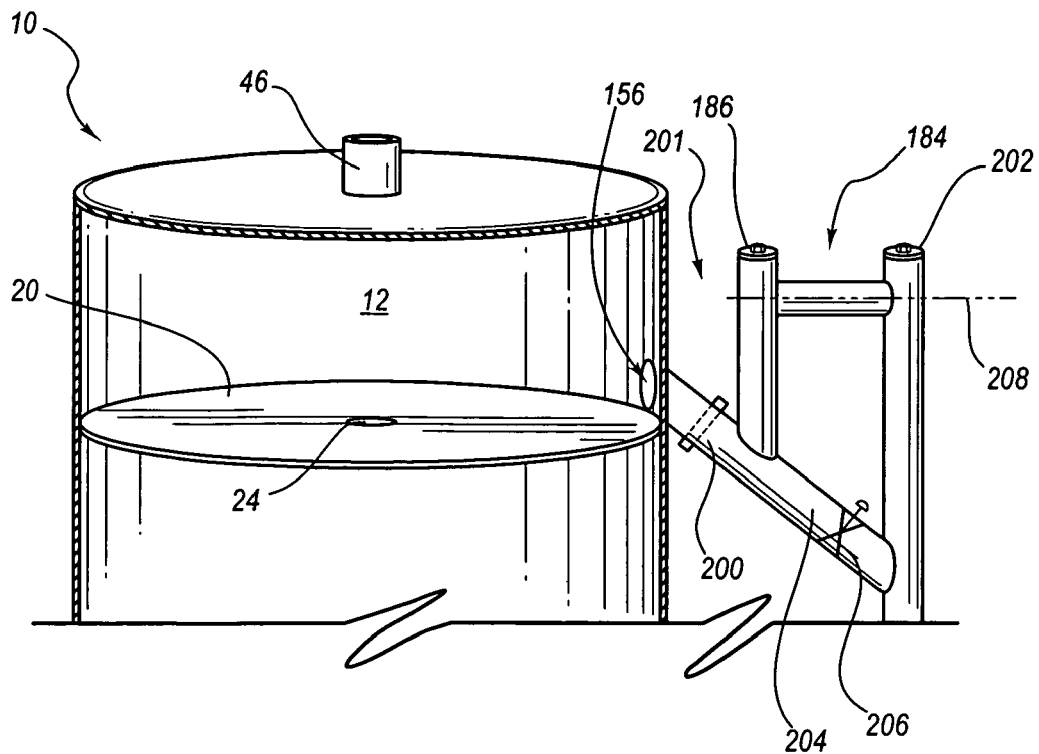
FIG. 11 is a partial front elevation view, including a broken away portion showing interior portions, of the bioreactor of FIG. 1 with a generally flat septum according to one embodiment of the present invention.

Another embodiment of the present invention is shown in FIG. 11. The embodiment of FIG. 11 is similar to the embodiment of FIG. 9, and may include other septum arrangements and modified piping at a first outlet 201. According to the embodiment of FIG. 11, rather than having a downward slope from an apex 80 (FIG. 9) to the vessel 12 side wall, the septum 20 is arranged substantially flat within the vessel 12. The generally flat arrangement may maintain more solids and more bacteria in the lower zone of the vessel 12.

The generally flat arrangement of the septum according to FIG. 11 may be accompanied by the modified piping at the first outlet 201. The first outlet 201 includes the effluent port 156 and may include a downward sloping segment 200 leading to the inverted P-trap 184. The inverted P-trap 184 continues to have at least one cleanout 186, and may include a second cleanout 202. In addition, the first outlet 201 may comprise a bypass 204 with a valve 206 disposed therein. The bypass 204 allows effluent to bypass the inverted P-trap 184 if the valve 206 is open. However, the valve 206 is normally closed during operation, and any solids that pass the septum 20 tend to fall out in the downward sloping segment 200 toward the valve 206 as the liquids pass through the inverted P-trap 184. The clean outs 186, 202 may be used to remove any accumulated solids.

According to the embodiment of FIG. 11, the effluent port 156 is substantially located just above the septum. Further, the centerline 181 of the top of the inverted P-trap 184 is arranged at an elevation higher than the generally flat septum 20. Therefore, liquids that have passed through the aperture 24 and collect on the top of the septum 20 tend to build up until the fluid level is sufficient to pass through the inverted P-trap 184. Again, any solids trapped in the exiting fluids will tend to "fall out" of the liquids toward the valve 206 of the bypass 204, rather than potentially plugging the inverted P-trap 184. The centerline 181 of the top of the P-trap 184 may be arranged approximately ten to twenty inches above the septum 20. For example, the centerline 181 of the top of the P-trap 184 may arranged approximately twelve inches above the septum 20. However, according to some embodiments, the centerline 181 of the top of the P-trap 184 may be arranged approximately one to three inches above the septum 20.

As in some of the previous embodiments, the inverted P-trap 184 shown in FIG. 11 prevents produced biogas from venting or leaving the vessel 12 through the effluent piping under normal circumstances. Instead, biogas is directed through the gas port 46. In addition, the inverted P-trap 184 protects against biogas overpressure. If biogas pressure within the vessel 12 increases to a predetermined measurement, the pressure will cause the fluid level on the septum 20 to decrease and expose the first effluent port 156 to the biogas. The excess pressure is then vented to atmosphere, maintaining the integrity of the vessel 12. According to some embodiments, the predetermined pressure that will expose the first effluent port 156 is approximately one to twenty inches of water, minus the diameter of the first effluent port 156.

According to some embodiments, the predetermined pressure is approximately ten to twenty inches of water, or approximately twelve inches of water.

Figure 12:
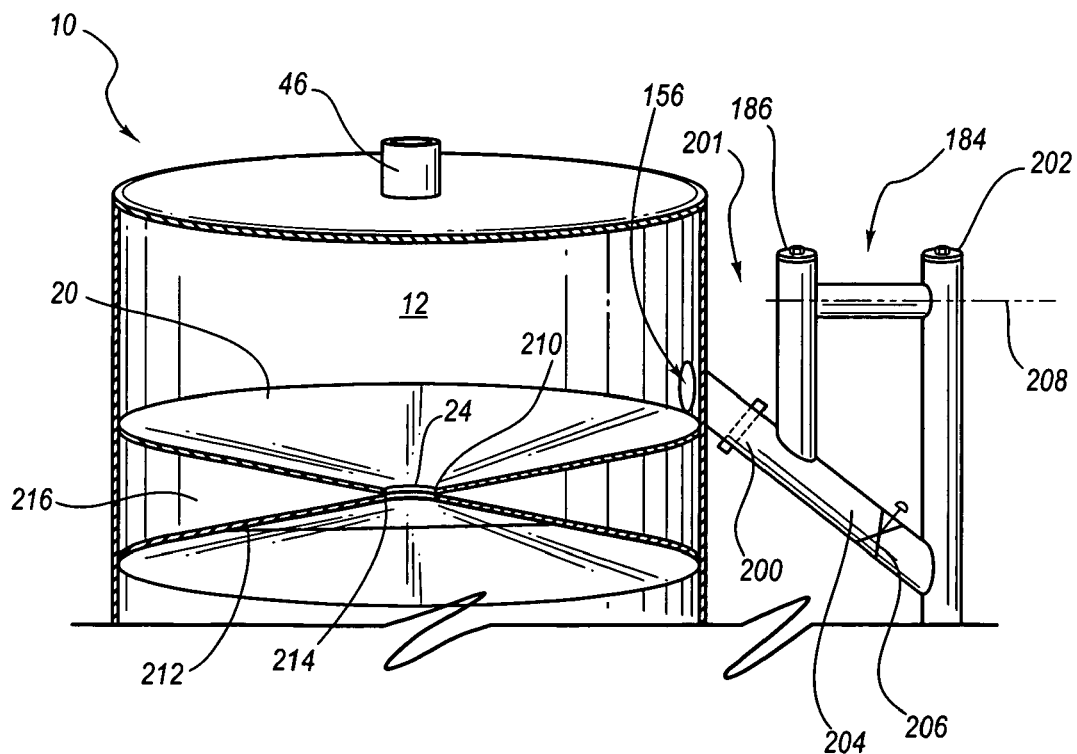
FIG. 12 is a partial front elevation view, including a broken away portion showing interior portions, of the bioreactor of FIG. 1 with a generally inverted septum according to one embodiment of the present invention.

Yet another embodiment of the present invention is shown in FIG. 12. The embodiment of FIG. 12 is similar to the embodiment of FIG. 9, and may include another septum arrangement and the modified outlet piping shown in FIG. 11. According to the embodiment of FIG. 12, the septum 20 has an upward or cupping slope from a lowest portion 210 to the side wall of the vessel 12. The septum 20 shown in FIG. 12 may be accompanied by a support. For example, the septum 20 may be accompanied by a generally flat plate 212. The generally flat plate 212 includes an aperture 214 substantially aligned with the aperture 24 of the septum 20. The generally flat plate 212 may also comprise a downward slope opposite of the upward slope of the septum 20 of FIG. 12. The generally flat plate 212 contacts and is attached to the septum 20, and encloses an area 216 disposed between the septum 20 and the generally flat plate 212.

The cupping arrangement of the septum 20 according to FIG. 12 may include the same or similar modified piping described above with reference to FIG. 11. Therefore, the first outlet 201 includes the effluent port 156 and the downward sloping segment 200 leading to the inverted P-trap 184. The other aspects of the first outlet 201 are also included as described with reference to FIG. 11.

According to FIG. 12, the effluent port 156 is again located just above the septum 20 at the side wall of the vessel 12. Further, the centerline 181 of the top of the inverted P-trap 184 is arranged at an elevation higher than the highest point of the septum 20 (which is at the side walls of the vessel). Therefore, liquids that have passed through the aperture 24 and sit on the top of the septum 20 tend to build up until the fluid level is sufficient to pass through the inverted P-trap 184. Any solids trapped in the exiting fluids will tend to "fall out" of the liquids back toward the apertures 24, 214 or, if they exit the effluent port 156, toward the valve 206 of the bypass 204. The centerline 181 of the top of the P-trap 184 may be arranged approximately ten to twenty inches above the highest points of the septum 20. For example, the centerline 181 of the top of the P-trap 184 may arranged approximately twelve inches above the septum 20. However, according to some embodiments, the centerline 181 of the top of the P-trap 184 may arranged approximately one to three inches above the septum 20.

While this invention has been described with reference to certain specific embodiments and examples, those skilled in the art will recognize that many variations are possible without departing from the scope and spirit of this invention. The invention, as defined by the claims, is intended to cover all changes and modifications of the invention which do not depart from the spirit of the invention. The words "including" and "having," as used in the specification, including the claims, shall have the same meaning as the word "comprising."

The invention claimed is:

1. An induced sludge blanket anaerobic reactor, comprising:
   a vessel configured to hold and maintain an anaerobic fluid mixture at a fluid level within the vessel, the anaerobic fluid mixture comprising water and organic solids;
   an inlet coupled to the vessel, the inlet configured to introduce a biodegradable biomass into the vessel;
   a first outlet coupled to the vessel, the first outlet configured to direct treated fluids to the outside of the vessel;

a gas port coupled to the vessel, the gas port configured to collect gasses produced in the vessel;

a septum having a periphery that is positioned below the fluid level, the septum positioned within the vessel to maintain solid particles below the septum;

an aperture formed in the septum that allows fluids to pass from below the septum to above the septum; and a plug control mechanism positioned within the septum.

2. An induced sludge blanket anaerobic reactor according to claim 1 wherein the septum tapers from an apex to side walls of the vessel.

3. An induced sludge blanket anaerobic reactor according to claim 1 wherein:

the septum tapers from an apex to a side wall of the vessel;

the first outlet is coupled to the side wall of the vessel at an elevation between the apex and the periphery of the septum at the side wall.

4. An induced sludge blanket anaerobic reactor according to claim 1, further comprising a second outlet coupled to the vessel adjacent to the first outlet, wherein:

the septum tapers from an apex to a side wall of the vessel;

the first outlet is coupled to the side wall of the vessel at a first elevation between the apex and the periphery of the septum at the side wall;

the second outlet is coupled to the side wall of the vessel at a second elevation.

5. An induced sludge blanket anaerobic reactor according to claim 1, further comprising a second outlet coupled to the vessel adjacent to the first outlet wherein:

the septum tapers from an apex to a side wall of the vessel;

the first outlet is coupled to the side wall of the vessel at an elevation between the apex and the periphery of the septum at the side wall;

the second outlet is coupled to the side wall between the first outlet and the periphery of the septum at the side wall.

6. An induced sludge blanket anaerobic reactor according to claim 1, further comprising a second outlet coupled to the vessel adjacent to the first outlet wherein:

the septum tapers from an apex to a side wall of the vessel;

the first outlet is coupled to the side wall of the vessel at an elevation between the apex and the periphery of the septum at the side wall;

the second outlet is coupled to the side wall between the first outlet and the periphery of the septum at the side wall;

the first and second outlets are fluidly connected in series and to a recirculation pump capable of moving solids from above the septum back into the vessel below the septum.

7. An induced sludge blanket anaerobic reactor according to claim 1 wherein the septum is generally flat.

8. An induced sludge blanket anaerobic reactor according to claim 1 wherein:

the septum slopes upward from an inverted apex to a side wall of the vessel.

9. An induced sludge blanket anaerobic reactor according to claim 1 wherein the first outlet comprises a gas trap and overpressure device.

10. An induced sludge blanket anaerobic reactor according to claim 1 wherein the first outlet comprises a gas trap and overpressure device, the gas trap and overpressure device comprising an inverted P-trap.

11. An induced sludge blanket anaerobic reactor according to claim 1 wherein:

the septum tapers from an apex to a side wall of the vessel;

the first outlet comprises a gas trap and overpressure device, the gas trap and overpressure device comprising an inverted P-trap, wherein a center of a top of the inverted P-trap is located at an elevation approximately equal to the apex.

12. An induced sludge blanket anaerobic reactor according to claim 1 wherein the first outlet comprises a gas trap and overpressure device, the gas trap and overflow device comprising an inverted P-trap with a cleanout.

13. An induced sludge blanket anaerobic reactor according to claim 1 wherein the first outlet comprises a gas trap and overpressure device, wherein the gas trap and overpressure device release gas through the first outlet at a predetermined pressure.

14. An induced sludge blanket anaerobic reactor according to claim 1 wherein the first outlet comprises a passive gas trap and overpressure device, wherein the passive gas trap and overpressure device releases gas through the first outlet when gas pressure in the vessel above the septum reaches approximately ten to twenty inches of water.

15. An induced sludge blanket anaerobic reactor according to claim 1 wherein the first outlet comprises a passive gas trap and overpressure device, wherein the passive gas trap and overpressure device releases gas through the first outlet when gas pressure in the vessel above the septum reaches approximately twelve inches of water.

16. An induced sludge blanket anaerobic reactor according to claim 1, further comprising a distribution plate disposed in the vessel at the inlet.

17. An induced sludge blanket anaerobic reactor according to claim 1 wherein the inlet comprises a pipe extended into the vessel to a tee, the tee emptying into the vessel in two directions, and further comprising a distribution plate disposed in the vessel at one exit of the tee.

18. An induced sludge blanket anaerobic reactor according to claim 1, further comprising a distribution plate attached to a pedestal disposed in the vessel, the pedestal being attached to a floor of the vessel, wherein the pedestal is adjacent to but spaced from the inlet.

19. An induced sludge blanket anaerobic reactor according to claim 1 wherein:

the septum tapers from an apex to a side wall of the vessel, wherein the apex is elevated from the side wall by approximately one to three inches.

20. An apparatus according to claim 1, wherein the plug control mechanism comprises an auger.

21. An apparatus as in claim 20, further comprising a drive mechanism coupled to the auger, the drive mechanism being configured to rotate the auger against a flow of fluids from the bottom zone to the upper zone of the vessel.

22. An apparatus, comprising:

an induced sludge blanket anaerobic reactor, the reactor comprising:

a vessel having an anaerobic fluid mixture positioned therein, the anaerobic fluid mixture comprising water and organic solids;

a septum positioned within the vessel so as to form an upper zone and a bottom zone in the anaerobic fluid mixture, the bottom zone of the anaerobic fluid mixture having a higher concentration of organic solids compared to the upper zone of the anaerobic fluid mixture, wherein the septum has an aperture formed therein that provides fluid communication between the bottom zone and the upper zone of the anaerobic fluid mixture;

an inlet coupled to the vessel, the inlet having a biodegradable biomass therein and the inlet configured to introduce the biodegradable biomass into the bottom zone of the anaerobic fluid mixture;

a first outlet coupled to the vessel, the first outlet configured to direct treated fluids from the upper zone of the anaerobic fluid mixture to outside the vessel, the first outlet comprising a gas trap; and a gas port coupled to the vessel, the gas port configured to collect gasses produced in the vessel.

23. An apparatus according to claim 22 wherein the a gas trap comprises a P-trap.

24. An apparatus according to claim 22, further comprising a second outlet in fluid communication with the first outlet, and wherein the gas trap comprises an inverted P-trap.

25. An apparatus according to claim 22, further comprising a second outlet in fluid communication with the first outlet, the second outlet disposed at a lower elevation on the vessel than the first outlet and located above the septum, wherein the gas trap comprises an inverted P-trap.

26. An apparatus according to claim 22, further comprising a second outlet in fluid communication with the first outlet, the second outlet disposed at a lower elevation on the vessel than the first outlet and located just above the septum, wherein the gas trap comprises an inverted P-trap with a cleanout, wherein the second outlet leads to a recirculation pump in fluid communication with the vessel below the septum.

27. An apparatus as in claim 22, further comprising an auger positioned within the aperture.

28. An apparatus, comprising:
an induced sludge blanket anaerobic reactor, the reactor comprising:
a vessel;
an inlet coupled to the vessel, the inlet introducing wastewater into the vessel;
a septum having a periphery, the septum positioned within the vessel to maintain solid particles below the septum;
an aperture formed in the septum inside the periphery;
a first outlet coupled to the vessel, the first outlet arranged above the septum and directing wastewater to the outside of the vessel, the first outlet comprising a gas trap and overpressure device;
a second outlet coupled to the vessel at an elevation lower than the first outlet and above the septum;
a gas port coupled to the vessel, the gas port collecting gasses produced in the vessel;
a distribution plate inside the vessel at the inlet.

29. A method of processing wastewater through anaerobic digestion, comprising:
sending a flow of wastewater into a vessel to hold wastewater;
anaerobically digesting the wastewater with bacteria;
retaining solids from the wastewater in a lower zone of the vessel with a septum;
releasing gases generated in the lower zone of the vessel through an aperture in the septum;
controlling plugging of the aperture;
trapping gas at an effluent outlet to the vessel;
collecting the gases generated in the lower zone of the vessel;
protecting against overpressure of the collected gases.

30. A method of processing wastewater through anaerobic digestion according to claim 29, further comprising recirculation solids that pass through the aperture back to the lower zone.

31. An apparatus, comprising:
an induced sludge blanket anaerobic reactor, the reactor comprising:
a vessel;
an inlet coupled to the vessel, the inlet configured to introduce wastewater into the vessel;
a first outlet coupled to the vessel, the first outlet configured to direct wastewater to the outside of the vessel;
a gas port coupled to the vessel, the gas port configured to collect gasses produced in the vessel;
a septum arranged substantially flat within the vessel, the septum maintaining solid particles therebelow, the septum positioned within the vessel to maintain solid particles below the septum;
an aperture formed in the septum; and
wherein the first outlet comprises a gas trap and overpressure device.

32. An apparatus according to claim 31 wherein the gas trap and overpressure device comprise an inverted P-trap.

33. An apparatus according to claim 31 wherein the first outlet comprises:
a downward sloping segment;
an inverted P-trap, extending from the downward sloping segment;
wherein a center of a top of the inverted P-trap is located at an elevation higher than the septum.

34. An apparatus according to claim 31 wherein the first outlet comprises:
a downward sloping segment;
an inverted P-trap extending from the downward sloping segment;
a cleanout port disposed in the inverted P-trap;
a valved bypass downstream of the downward sloping segment and in fluid communication with the inverted P-trap.

35. An apparatus according to claim 31 wherein the first outlet comprises a passive gas trap and overpressure device, wherein the passive gas trap and overpressure device releases gas through the first outlet when gas pressure in the vessel above the septum reaches approximately ten to twenty inches of water.

36. An apparatus, comprising:
an induced sludge blanket anaerobic reactor, the reactor comprising:
a vessel;
an inlet coupled to the vessel, the inlet configured to introduce wastewater into the vessel;
a first outlet coupled to the vessel, the first outlet configured to direct wastewater to the outside of the vessel;
a gas port coupled to the vessel, the gas port configured to collect gasses produced in the vessel;
a septum arranged within the vessel, the septum maintaining solid particles therebelow, the septum comprising an upward slope from a lowest portion to a side wall of the vessel;
an aperture formed in the septum; and a plate disposed below and contacting the septum.

37. An apparatus according to claim 36, further comprising a generally flat plate under the septum, the generally flat plate comprising an aperture aligned with the aperture of the septum, the generally flat plate cooperating with the septum to enclose an area between the generally flat plate and a sloping surface of the septum.

38. An apparatus according to claim 36 wherein the first outlet comprises:
- a downward sloping segment;
- an inverted P-trap extending from the downward sloping segment;
- wherein a center of a top of the inverted P-trap is located at an elevation higher than the septum.

39. An apparatus according to claim 36 wherein the first outlet comprises:
- a downward sloping segment;
- an inverted P-trap, extending from the downward sloping segment;
- a cleanout port disposed in the inverted P-trap;
- a valved bypass downstream of the downward sloping segment and in fluid communication with the inverted P-trap.

* * * * *